(12) United States Patent
Liu

(10) Patent No.: US 10,605,752 B2
(45) Date of Patent: Mar. 31, 2020

(54) METHOD AND DEVICE FOR MEASURING A TRANSITION RATE OF A PHASE TRANSITION

(71) Applicant: Jin-Chen Liu, Dachau (DE)

(72) Inventor: Jin-Chen Liu, Dachau (DE)

(*) Notice: Subject to any disclaimer, the term of this patent is extended or adjusted under 35 U.S.C. 154(b) by 314 days.

(21) Appl. No.: 15/364,975

(22) Filed: Nov. 30, 2016

(65) Prior Publication Data
US 2017/0160216 A1 Jun. 8, 2017

(30) Foreign Application Priority Data
Dec. 2, 2015 (DE) .................. 10 2015 120 899

(51) Int. Cl.
| | | |
|---|---|---|
| *G01K 17/00* | (2006.01) | |
| *G01N 25/02* | (2006.01) | |
| *H01L 35/32* | (2006.01) | |
| *G01N 25/48* | (2006.01) | |
| *G01N 33/00* | (2006.01) | |
| *G01K 7/02* | (2006.01) | |
| *G01L 13/00* | (2006.01) | |
| *G01N 15/08* | (2006.01) | |

(Continued)

(52) U.S. Cl.
CPC ............ *G01N 25/02* (2013.01); *G01K 7/021* (2013.01); *G01L 13/00* (2013.01); *G01N 15/08* (2013.01); *G01N 25/48* (2013.01); *G01N 33/0098* (2013.01); *H01L 35/32* (2013.01); *A61B 5/4266* (2013.01); *A61B 2562/029* (2013.01); *A61B 2562/0271* (2013.01); *G01N 33/367* (2013.01)

(58) Field of Classification Search
None
See application file for complete search history.

(56) References Cited

U.S. PATENT DOCUMENTS 4,312,218 A * 1/1982 Eckles ................ G01N 15/08
702/2
5,269,183 A * 12/1993 Van Bavel ............... G01F 1/68
73/204.22

(Continued)

FOREIGN PATENT DOCUMENTS

DE    10 2005 061 411 A1    6/2007

OTHER PUBLICATIONS

Search Report of European Patent Office issued in Application No. 16 20 0346 with English translation of category of cited documents dated Jul. 5, 2017 (15 pages).

(Continued)

*Primary Examiner* — Lisa M Caputo
*Assistant Examiner* — Nasir U. Ahmed
(74) *Attorney, Agent, or Firm* — Flynn Thiel, P.C.

(57) ABSTRACT

A method and a device for measuring a transition rate between a first phase of a material and a second phase of the material wherein the material is solid or liquid in the first phase and gaseous in the second phase. A thermopile which includes a plurality of conductor transitions at an interface area between the first and second phases. The thermopile has a first portion which includes every second one of the conductor transitions, and a second portion that includes the remaining conductor transitions. In addition, the method includes measuring a thermoelectric voltage that is applied on the thermopile and that represents a temperature difference between the first and second portions of the thermopile.

14 Claims, 4 Drawing Sheets

(51) Int. Cl.
    *A61B 5/00*     (2006.01)
    *G01N 33/36*    (2006.01)

(56) References Cited

U.S. PATENT DOCUMENTS

| | | | |
|---|---|---|---|
| 7,631,538 B2 * | 12/2009 | Imhof | G01N 25/56 |
| | | | 73/24.04 |
| 2006/0070650 A1 | 4/2006 | Fraden | |
| 2008/0273572 A1 | 11/2008 | Lawrence et al. | |
| 2010/0086005 A1 | 4/2010 | Blokland | |

OTHER PUBLICATIONS

Susan Steinberg, et al. Article Entitled "A Gauge to Measure Mass Flow Rate of Sap in Stems and Trunks of Woody Plants", J. Amer. Soc. Hort. Sci. 114(3):466-472 1989.

Search Report of Chinese Patent Office issued in Application No. 201611096577.2 dated Jan. 21, 2019 (6 pages).

Search Report of German Patent Office issued in Application No. 10 2015 120 899.7 dated Oct. 24, 2016 (12 pages).

Boyer, John S., Measuring the water status of plants and soils. Chapter 3. Thermocouple Psychrometer. Academic Press, Inc. 1995 (54 pages).

Haines, F.M., Transpiration and Pressure Deficit. III. Observations by the Thermopile Method. Annals of Botany, 1936, Nr. 1, S. (pp. 1-22).

Impens, I. I. et al. Diffusive resistances at, and Transpiration Rates from Leaves in Situ Within the Vegetative Canopy of a Corn Crop. Plant physiology, 1967, 42. Jg., Nr. 1, S. (pp. 99-104).

\* cited by examiner ns in the gas
METHOD AND DEVICE FOR MEASURING A TRANSITION RATE OF A PHASE TRANSITION

CROSS-REFERENCE TO RELATED APPLICATIONS

This claims priority from German Patent Application No. 10 2015 120 899.7, filed Dec. 2, 2015, the disclosure of which is hereby incorporated by reference in its entirety into this application.

FIELD OF THE INVENTION

The present invention relates to a method and a device for measuring a transition rate between a solid or liquid phase of a material and a gaseous phase of the material. Particularly advantageously, the invention can be applied to the measurement of a transition rate of a phase transition, in particular a liquid-gaseous phase transition of water. However, the invention can also be applied for measuring the transition rate between phases of other materials such as alcohol.

A series of physical quantities can be determined based on the speed of a phase change of a material. The invention therefore also relates to applications of the method and the device for measuring the transition rate of the phase transition.

BACKGROUND OF THE INVENTION

A device for measuring the steam flux from a surface is known from U.S. Pat. No. 7,631,538 B2. More specifically, the surface is human skin whose water loss rate is to be determined. A first end of a small tube is put on the surface. By means of atmospheric humidity sensors that are spaced from one another in the extending direction of the small tube, the moisture gradient in the small tube is measured. Then, the steam flux away from the surface can be calculated with the obtained data.

A so-called porometer for measuring the transpiration of plant leaves is known from U.S. Pat. No. 4,312,218 A. A leaf to be measured is enclosed in a chamber. Then, a current of dry air into the chamber is controlled in a way that the atmospheric humidity in the chamber remains constant. The transpiration of the leaf can eventually be determined from the flow speed of the air.

SUMMARY OF THE INVENTION

The described known methods are each based on a dynamic measurement of the water concentration in the gas phase in order to characterize a liquid-gaseous phase transition of water. Such an indirect determination of the transition rate can be relatively time-consuming and can react very sensitively to external conditions.

Therefore, a purpose of the present invention is to provide a method and a device for measuring a transition rate of a phase transition between a solid or liquid and a gaseous phase of a material that allow for a measurement that is as easy as possible, reliable and direct.

This problem is solved by the subject matter of claims 1, 9 and 13. The dependent claims describe advantageous embodiments of the invention.

The invention provides a method and a device for measuring a transition rate between a first phase of a material and a second phase of the material. In the first phase, the material exists in a solid or liquid state. In the second phase, the material is in a gaseous state.

The invention allows for a measurement of the transition rate directly at an interface area between the first and the second phases. By means of the method and/or the device according to the invention, an actual transition rate between the two phases of the material can be determined as a physical quantity, for example in the unit [mol/(m^2*s)] (in relation to the measured section of the interface area). Depending on the application, however, this can be relatively time-consuming because it might require calibration measurements or reference values under known conditions. For some applications, it is sufficient to measure a quantity (for example the thermoelectric voltage described in the following) that is, for example, proportional to the actual transition rate, out of which the transition rate can be determined while implementing appropriate calibration measurements, or that allows for a comparison of different measured transition rates. Within the meaning of the present invention, also the determination of such a quantity can be regarded as "measuring the transition rates" between the phases without engaging in an explicit quantification of the actual transition rate.

The present invention is based on a measurement of the temperature difference that exists at the interface area between the phases due to a latent heat (evaporation or condensation heat and/or sublimation or resublimation heat) of the phase transition.

To measure the temperature difference, according to the inventive method, a thermopile is provided at the interface area between the first and the second phases.

Thermopiles use the thermoelectric effect for temperature measurement and are for example known from applications in radiation detectors. They comprise several thermoelements that are connected thermally in parallel and electrically in a row. The sum of the partial voltages generated by the individual thermoelements can be tapped between the two ends of the thermopile as a thermoelectric voltage by means of a voltage measurement device. The thermopile comprises a plurality of conductor elements for example in form of individual wires or wire segments. Conductor elements made of two different materials, for example constantan and copper or tellurium and antimony, which are arranged alternatingly in a row to form the thermopile, are provided. Successive conductor elements made of different materials are respectively connected to one another at conductor transitions and form a thermoelement of the thermopile. The thermopile comprises a first portion that comprises every second one of the conductor transitions, and a second portion that comprises the remaining conductor transitions. Preferably, the first portion and the second portion are located opposite to one another, in particular they are disposed in parallel to one another. The thermoelectric voltage that is output by the thermopile represents a temperature difference between the first and the second portions of the thermopile.

According to the invention, the thermoelectric voltage of the thermopile that is provided at the interface area between the phases is measured. This thermoelectric voltage represents a temperature difference that exists due to the latent heat of the phase transition in the area of the phase interface and therefore allows for conclusions about the transition rate of the phase transition. Advantageously, the thermopile comprises a large number of thermoelements (i.e. many conductor transitions). As the partial voltages that are generated by the individual thermoelements that are switched in a row are added up, the typically very low temperature difference, which is generated by the latent heat of the phase transition, can be detected. It has proven to be advantageous for the thermopile to comprise at least 10, 50, 100, 500, 1000 or more than 1000 conductor transitions. It is logical that the thermopile used in the present invention can be composed of a plurality of shorter thermopiles that are switched in a row by means of connection elements.

The relationship between the measured thermoelectric voltage and the transition rate of the phase transition depends for example on the material to be measured and on the orientation of the thermopile with regard to the interface area. Those and further dependencies can be taken into account via calibration measurements on known systems in order to draw conclusions about the transition rate between the phases based on the thermoelectric voltage. But also without an explicit determination of the transition rate, statements can already be made based on the measured thermoelectric voltage, for example if transition rates of different systems are to be compared. A high measured thermoelectric voltage (high temperature difference between the first and the second portions of the thermopile) indicates a high transition rate. Conversely, a low measured thermoelectric voltage (low temperature difference between the first and the second portions of the thermopile) can indicate a low transition rate.

According to an embodiment, the measured thermoelectric voltage is used in a method for determining a pressure potential p of one of the two phases. The pressure potential is a measure of the amount of energy that needs to be used or that will be obtained if a defined quantity of the material is fed to the phase. In this context, a negative pressure potential p indicates released energy during feeding of further material and a positive pressure potential p indicates energy to be used during feeding of further material. Without external influences, the material therefore typically diffuses from a region with a high pressure potential into a region with a low pressure potential. In a manner of speaking, the pressure potential of a phase indicates the receptivity for further material. The measurement of the pressure potential p of water, which is often called "water potential", has a particularly high number of applications. For example, there is a need for determining the water potential of different material compositions such as grounds, construction material, plants, foods, medicines or textiles.

The method for determining the pressure potential p of one of the two phases by using the measured thermoelectric voltage is based on the so-called Darcy's law. It stipulates that the transition rate of a material between a first region and a second region is directly proportional to the difference of the pressure potentials of the material in the two regions. If the material exists in the first phase in the first region and if it exists in the second phase in the second region, Darcy's law can be applied to the transition rate between the first and the second phases: $Vt=k*(p2-p1)$. Here, Vt is the transition rate from the first phase into the second phase (can be negative), p1 is the pressure potential of the first phase, p2 is the pressure potential of the second phase and k a proportionality factor. The transition rate Vt can be determined out of the measured thermoelectric voltage. The proportionality factor k is dependent on the permeability of the interface area and can be determined by means of suitable reference measurements. Therefore, the pressure potentials p1, p2 of the first phase or the second phase can be determined by means of Darcy's law and based on a known or measured value of the pressure potential p1, p2 of the other phase of the material if the thermoelectric voltage has been measured. If the pressure potential p1 of the first phase is to be determined, the required value of the pressure potential p2 of the gaseous phase of the material can for example be simply determined. For that, only a temperature and a moisture measurement are necessary. The pressure potential in the gaseous phase can then be determined as $p2=RT/\tilde{V}*\ln(\varphi)$ with R being the universal gas constant, T the temperature in K, $\tilde{V}$ the molar volume of the material in the liquid state and $\varphi$ the relative moisture in the gaseous phase. The relative moisture in the gaseous phase p is thereby defined for all materials analogously to the "relative atmospheric humidity" in case of water.

According to another embodiment, the measured thermoelectric voltage can be used to determine a permeability of a separation layer, in particular a film or a textile layer. In this process, the separation layer is positioned in a way that it exists during measurement of the thermoelectric voltage between the first phase and the second phase so that the material has to pass the separation layer during the phase transition. The permeability of the separation layer can be determined out of the proportionality factor k from Darcy's law. Hence, the permeability of the separation layer can be determined based on the measured thermoelectric voltage if the values of the pressure potentials p1, p2 of the two phases of the materials are known in addition. A permeability measurement can be performed particularly easily if a liquid with a known pressure potential p1 is used as a first phase and if the pressure potential p2 in the gaseous phase is determined, as described above, by means of a temperature and a moisture measurement.

Depending on the application, different positioning variants of the thermopile at the interface area between the phases are possible. In any case, it can be advantageous to position the thermopile as closely as possible to the interface area because the latent heat is released or absorbed at the interface area. In particular, the thermopile, more specifically its first or second portion, can be situated at a distance of less than 1 μm, 20 μm, 1 mm, 5 mm, 1 cm or less than 2 cm from the interface area.

According to a variant (type A), the thermopile can be provided at the interface area in such a way that its first portion exists within the first phase and its second portion exists within the second phase. This is in particular advantageous for measuring a liquid-gaseous transition because the first portion of the thermopile can simply be inserted into the liquid phase in this case. For example, this is how the evaporation rate of a water surface can be determined.

According to another variant (type B), the thermopile is arranged completely on the side of the interface area that corresponds to the first phase or to the second phase. Hence, the thermopile is completely within the first or the second phase. According to this embodiment, the first portion of the thermopile is positioned more closely to the interface area than the second portion of the thermopile so that the temperature difference, which exists perpendicularly to the interface area due to the latent heat, can be measured based on the thermoelectric voltage of the thermopile. Such an arrangement is particularly advantageous when a phase is located in a region that is difficult to access such as water (liquid phase) in a building wall. Then, the thermopile can be disposed outside of the region that is difficult to access, for example in the gaseous phase outside of the building wall. For example, the water potential outside of the building wall could be determined by means of a moisture and temperature sensor and then the water potential of the building wall could be determined in consideration of the measured thermoelectric voltage of a thermopile, which is positioned on or attached to the building wall, by means of Darcy's law.

According to a further variant (type C), the thermopile is provided at the interface area in such a way that its first portion and its second portion are located in a common plane that is parallel to the interface area. Therefore, no temperature difference due to the latent heat of the phase transition would be detectable in principle as both portions of the thermopile are located at the same distance to the interface area. In order to still enable a measurement, the interface area is covered with a cover at the first portion of the thermopile according to the invention, but not at the second portion of the thermopile. The cover can be positioned between the first portion of the thermopile and the interface area or on the side of the first portion of the thermopile that is located opposite to the interface area. Through the cover, a transition between the first and the second phases of the material at the first portion of the thermopile is suppressed or prevented. Consequently, no or a lower quantity of latent heat is released or extracted there. At the second portion of the thermopile, however, the phase transition can take place in an undisturbed way and latent heat can be released or extracted. Hence, also in case of a thermopile that is provided flatly on the interface area, a transition rate between the phases can be measured by measuring the thermoelectric voltage. As, according to this embodiment, the first and the second portions of the thermopile are located in a common plane that is parallel to the interface area, an external temperature gradient that exists perpendicularly to the interface area independently of the phase transition cannot distort the measurement. This is for example advantageous for a measurement at a ground surface because the vertical temperature gradient, which might come from a ground surface that is possibly heated by the incidence of sunlight, will not affect the measurement.

In some applications, a "natural" interface area between the solid or liquid first phase and the gaseous second phase already exists in the system to be measured and the measurement method described above can be performed without further ado. Examples for this are the measurement of the evaporation at a water surface and the measurement of the transpiration of a living being.

A device according to the invention pursuant to an embodiment allows for a particularly easy-to-perform measurement of the transition rate at a natural interface area between a first, solid or liquid, phase and a second, gaseous, phase. The device comprises an adhesive layer with a lower side and an upper side, whereby the lower side can be attached to an interface area between the first and second phases of the material. The interface area can for example be the skin of a user whose transpiration rate is to be measured. Also the attachment on a plant or parts of a plant for determining the transpiration rate of such plant is possible. For example, the device can be attached on a transpiring lower side of a leaf via the lower side of the adhesive layer. To perform the measurement, the thermopile with the plurality of conductor transitions is attached to the adhesive layer, wherein the thermopile has a first portion, which comprises every second one of the conductor transitions, and a second portion, which comprises the remaining conductor transitions, and is designed to emit a measurable thermoelectric voltage that represents a temperature difference between the first and second portions of the thermopile.

Such a device can be particularly advantageous for performing measurements of type C. For that, the first portion and the second portion of the thermopile can be located in a common plane that is parallel to the upper side of the adhesive layer, wherein a cover, which covers the adhesive layer at the first portion of the thermopile but not at the second portion of the thermopile, is provided. But also other arrangements of the thermopile at the adhesive layer are possible, for example to perform measurements of types A and B.

A device according to the invention pursuant to a further embodiment is particularly suitable for measuring a transpiration rate of a plant leaf. Also with this device, a transition rate between a first phase of a material and a second phase of the material can be measured, wherein the material exists in a solid or liquid state in the first phase and in a gaseous state in the second phase. In the application to the plant leaf, water (material) within the leaf is liquid (first phase) and passes to the gaseous state outside of the leaf (second phase) during transpiration of the leaf on a lower leaf side (interface area).

The device according to this embodiment comprises the thermopile with a plurality of conductor transitions, wherein the thermopile has a first portion, which comprises every second one of the conductor transitions, and a second portion, which comprises the remaining conductor transitions, and is designed to emit a measurable thermoelectric voltage that represents a temperature difference between the first and second portions of the thermopile. According to the embodiment in question, a slit for receiving a sample that comprises an interface area between the first phase and the second phase exists between the first portion and the second portion of the thermopile. In particular, a plant leaf can be received in the slit. The first portion of the thermopile will then be adjacent to the lower leaf side and the second portion of the thermopile adjacent to the upper leaf side. As plant leaves typically transpire only on one side (usually on the lower side), a temperature difference, which arises due to the latent heat of the phase transition through the transpiration on only one leaf side, can be measured between the upper leaf side and the lower leaf side based on the thermoelectric voltage at the thermopile. The transpiration rate can therefore be determined.

The invention also provides a possibility to perform measurements in systems in which there is at first no boundary between a solid or liquid phase and a gaseous phase. To be able to measure a transition rate between two regions, in each of which the material is in a gaseous state, (e.g. in order to determine a pressure potential), the first phase can be created artificially, in particular as a liquid phase. This can be achieved by providing a porous substrate plate. It is a known phenomenon that gaseous material condenses more easily within a porous substrate due to effects of surface tension. This effect scales with the diameter of the pores of the substrate. The mean pore diameter of the substrate is preferably larger than the diameter of a molecule of the material to be measured but smaller than 100 μm. For example, to make steam condense, a porous substrate with a mean pore diameter in the range of several nanometers up to several micrometers can be provided. Mean pore diameters of less than 100 μm, less than 50 μm, less than 10 μm, less than 1 μm or less than 800 nm or a mean pore diameter between 200 nm and 800 nm, between 500 nm and 2 μm or between 200 nm and 5 μm are particularly advantageous.

The porous substrate plate separates a first region in which the material is in a gaseous state and a second region in which the material is in a gaseous state. Of course, the substrate plate should be permeable for the material. This can be achieved by the substrate plate having pores that are continuously linked to one another from its upper side to its lower side and through which the material can pass. Alternatively, the pores can for example be provided only on the lower side and/or the upper side of the substrate plate, in particular as open pores. In this case, the substrate plate can be made of or comprise a raw material that is permeable for the material.

To diffuse from one region into the other region, the material has to pass through the substrate plate. In this process, the material condenses within the substrate plate so that a liquid phase is artificially created there. Then, the transition rate from this liquid phase (first phase) into the gaseous phase (second phase) of a region can be determined by means of a thermopile, analogously to the method described above. This transition rate allows for determining the transition rate between the two regions. Hence, a transition rate between a (artificially created) first, solid or liquid, phase and a second, gaseous, phase of a material is measured also in this case.

It will be particularly advantageous if the thermopile is already integrated firmly in the artificial interface area and/or attached to such interface area. In this case, the orientation and positioning of the thermopile in relation to the interface area is constant over several measurements. As also the permeability properties of the interface area are constant (and in addition adjustable by selecting an appropriate porous substrate plate), calibration measurements that are performed once and reference data obtained from such measurements can be used in a simple way for multiple measurements.

A device according to the invention for measuring the transition rate between a first phase of a material and a second phase of the material according to an embodiment provides such a porous artificial interface area with a thermopile installed on it. Also with regard to the description of the device, the material should exist in a solid or liquid state in the first phase and in a gaseous state in the second phase.

The device according to the invention is suitable for performing the method according to the invention. Features described in relation to the method can of course be transferred to the device and vice versa.

The device for measuring the transition rate comprises a porous substrate plate with a lower side and an upper side. Advantageous properties with regard to the pore size have already been described.

The thermopile with a plurality of conductor transitions is installed at the porous substrate plate. As explained above, the thermopile comprises a first portion, which comprises every second one of the conductor transitions, and a second portion, which comprises the remaining conductor transitions, and is designed to output a measurable thermoelectric voltage that represents the temperature difference between the first and the second portions.

Also in case the first phase is created artificially, measurements are possible with all the positioning variants of the thermopile (type A, type B and type C) described above. In this context, it shall be noted that the interface area between the liquid first phase in the pores and the gaseous second phase will not have to form a continuous interface area anymore if the porous substrate plate is used. The principles of positioning the thermopile in relation to the interface area, which were explained above, however, can be transferred as follows to the positioning of the thermopile in relation to the porous substrate plate as the interface area can be regarded as extending approximately within the substrate plate in parallel to the lower side and/or the upper side of such substrate plate. To be able to perform measurements of type A, the first portion of the thermopile can be provided on the lower side of the substrate plate and the second portion of the thermopile on the upper side of the substrate plate (device type A).

To be able to perform measurements of type B, the thermopile can be located completely on the lower side or completely on the upper side of the substrate plate, wherein the first portion of the thermopile is located more closely to the respective side of the substrate plate than the second portion of the thermopile (device type B). In particular, the first portion of the thermopile can be attached directly on the porous substrate plate.

To be able to perform a measurement of the type C, the first and the second portions of the thermopile have to be located in a common plane that is parallel to the lower side and/or the upper side of the substrate plate (device type C). In this case, the device also comprises a cover that covers the porous substrate plate at the first portion of the thermopile but not at the second portion of the thermopile. Advantageously, the cover is provided between the upper side or the lower side of the substrate plate and the first portion of the thermopile. But the cover can also be provided on the side of the thermopile that is opposite to the substrate plate. In particular, the cover can be attached on the substrate plate and/or the thermopile. The thermopile can be installed flatly on the respective side of the substrate plate.

To create a defined measurement environment, the substrate plate with the thermopile (type A, type B or type C) can be provided or installable in a tube in such a way that it divides the tube into two axially successive sections. Such an arrangement allows for a measurement of the water potential of a ground without any special work. For the measurement, the pipe is simply sunk into the ground up to the substrate plate. In the ground section within the lower section of the tube sunk into the ground, the water is typically in a gaseous state. In the upper section of the tube that stands out of the ground, the water is also gaseous in form of atmospheric humidity. As described above, a phase of liquid water is formed due to the porous structure in the porous substrate plate. By measuring the thermoelectric voltage at the thermopile, the transition rate of water between the lower section of the tube (ground) and the upper section of the tube (air) can therefore be measured (indirectly and based on the passage rate from the or into the artificially created liquid phase) as also described above. This is evidently an example for a measurement of a passage rate of water between two regions in which water exists in a gaseous state. Based on a temperature and moisture measurement in the section of the tube that stands out of the ground, the water potential of the upper gas phase can be determined as described above. For this purpose, a moisture and temperature sensor can be provided on the tube. Then, the water potential of the ground can be determined by means of Darcy's law.

Alternatively to the tube, the device can comprise a container with a floor for the implementation of other measurements. The substrate plate with the thermopile (type A, type B or type C) can be provided or installable in the container in such a way that it divides the receiving volume of the container into a lower part, which comprises the floor of the container, and an upper part that is in particular open. The lower part of the container can be designed to receive a sample whose water potential is to be determined. After a certain time, there will be an equilibrium and the water potential of the sample will be equivalent to the water potential of the gaseous phase in the lower part of the container. If there is also a gaseous phase of water (e.g. in air) in the upper part of the container, the water potential of the sample can be determined similarly to the measurement of the water potential of the ground with the tube. Therefore, the water potential of the gaseous phase in the upper part of the container can be determined by means of a moisture and temperature meter.

But it is also possible to perform a measurement of the transition rate between a liquid or solid first phase, which already exists, and a gaseous second phase by means of the device according to the invention with a substrate plate. An advantageous example of such a measurement is a variation of the described measurement of the water potential of the sample located in the lower part of the container. For this purpose, a water layer is introduced into the upper part of the container. The substrate plate separates the gaseous phase (second phase), which exists in the lower part of the container, from the water layer (first phase) in the upper part. In such a situation, the interface area between the phases can be regarded as parallel to the substrate plate. In addition, the interface area can be regarded as within the substrate plate or as located on the surface of such substrate plate. Through a measurement of the thermoelectric voltage of the thermopile provided on the substrate plate, the transition rate between the phases can then be determined. An advantage of the provision of the water layer in the upper part of the container is that the water potential in the upper part of the container is set to a known value, in particular to zero. Therefore, no moisture and temperature sensor has to be provided in order to determine the water potential of the sample.

The present invention also relates to the use of the described method or of the described device for measuring a transpiration rate of a living being, e.g. in defined stress situations such as while doing sports, for measuring an evaporation rate of a ground or for determining a water potential or a permeability of a material composition, in particular of a plastic film and/or a packaging material.

BRIEF DESCRIPTION OF THE DRAWINGS

In the following, the invention shall be described in greater detail based on embodiments by means of the enclosed drawings. The Figures show.

DETAILED DESCRIPTION

Figure 1A:
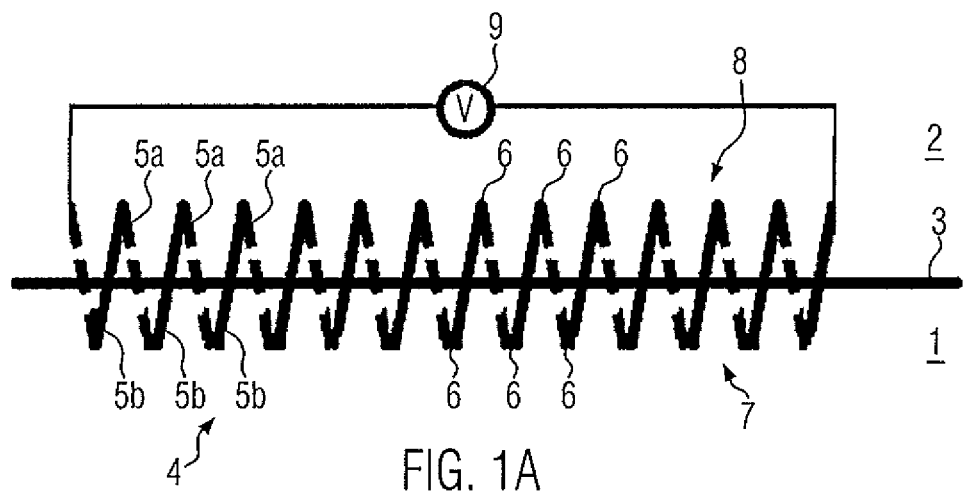
FIG. 1A a schematic sectional view of a measurement according to an embodiment of type A, wherein the section plane is perpendicular to the interface area between the phases.
Figure 1B:
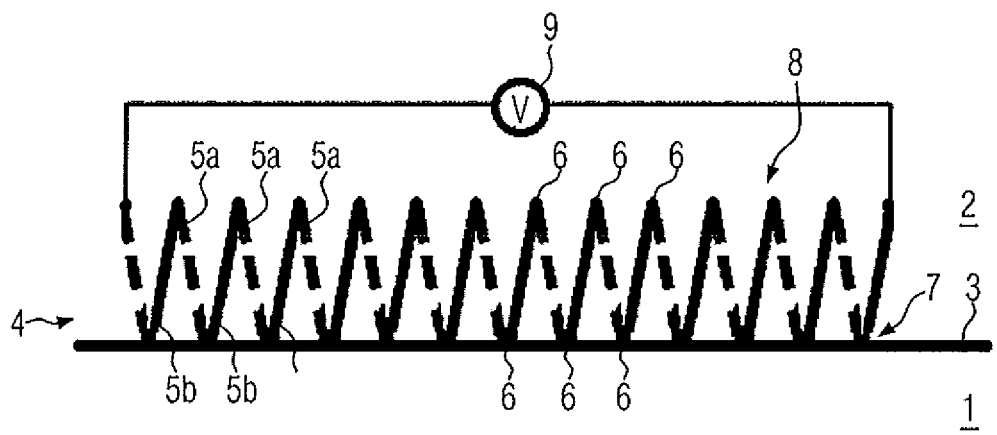
FIG. 1B a schematic sectional view of a measurement according to an embodiment of type B, wherein the section plane is perpendicular to the interface area between the phases.
Figure 1C:
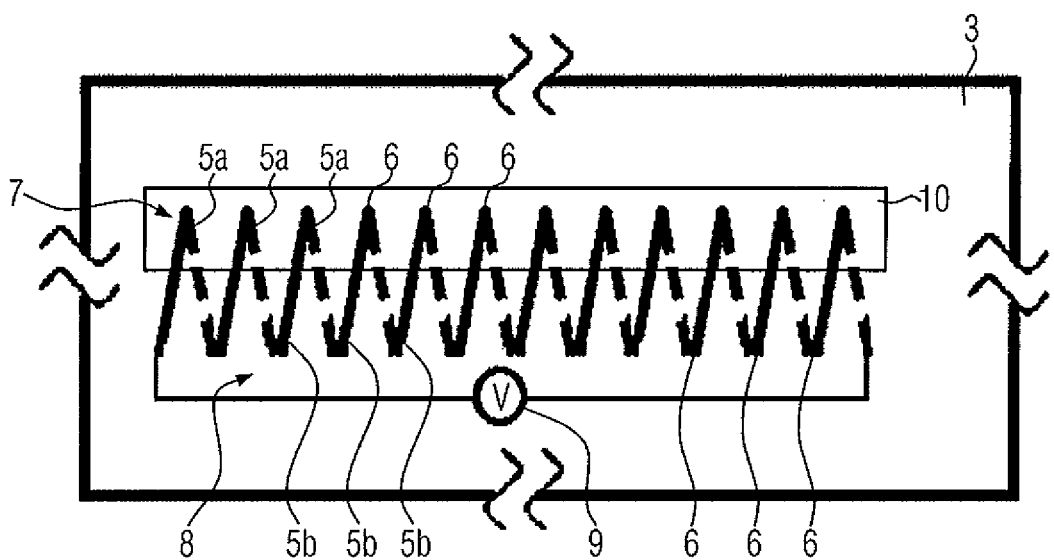
FIG. 1C a schematic display of a measurement according to an embodiment of type C in a top view on the interface area between the phases.

FIGS. 1A, 1B and 1C schematically illustrate different embodiments of a measurement according to the invention. In each case a transition rate between a first phase 1 and a second phase 2 of a material is measured. In the first phase 1, the material is in a solid or liquid state and in the second phase 2 it is gaseous. Hence, the material passes between the phases 1, 2 by way of evaporation/condensation or by way of sublimation/resublimation. In case of a transition from the first phase 1 to the second phase 2, latent heat is released or extracted from the environment at an interface area 3 between the phases 1, 2. Therefore, a temperature gradient is formed in the region of the interface area 3, in particular a temperature gradient that is perpendicular to the interface area 3. The invention takes advantage of this temperature gradient being a measure for the transition rate between the phases 1, 2 of the material and allowing for a determination of the transition rate.

The temperature difference that exists in the region of the interface area 3 due to the latent heat, is determined according to the invention with a thermopile 4. The thermopile 4 comprises a plurality of conductor elements 5a, 5b, wherein respectively conductor elements 5a made of a first material, for example constantan or tellurium, are connected alternatingly and successively with conductor elements 5b made of a second material such as copper or antimony. The connection points between two successive conductor elements 5a, 5b are referred to as conductor transitions 6. The thermopile 4 has a first portion 7, which comprises every second one of the conductor transitions 6, and a second 8 portion that comprises the remaining conductor transitions 6. A thermoelectric voltage between the ends of the thermopile 5 is measured by means of a voltage measuring device 9. This thermoelectric voltage represents a temperature difference between the first 7 and second 8 portions of the thermopile 4.

Through suitable positioning of the thermopile 4 at the interface area 3 between the phases 1, 2, the thermogradient that exists due to the latent heat can be measured based on the thermoelectric voltage of the thermopile 4 and hence the transition rate between the phases 1, 2 can be determined. In the Figures, thermopiles 4 with a relatively small number of conductor transitions 6 are displayed for reasons of clarity. In practice, it can be advantageous or necessary for the thermopile 4 to comprise a significantly larger number of conductor transitions 6 (e.g. at least 10, 50, 100, 500, 1000 or more than 1000) as also very low temperature differences can be measured that way. It is also logical that the thermopile 4 used in the present invention can be composed of a plurality of thermopiles 4 that are connected in a row by means of connecting elements.

Different variants are possible for suitably positioning the thermopile 4.

According to a variant (type A) shown in FIG. 1A, the thermopile 4 is provided at the interface area 3 in such a way that the first portion 7 of the thermopile 4 exists within the first phase 1 and the second portion 8 of the thermopile 4 within the second phase 2. Therefore, a temperature gradient that is perpendicular to the interface area 3 and that comes from the latent heat of the phase transition can be detected.

Another variant (type B) of positioning the thermopile 4 at the interface area 3 is shown in FIG. 1B. Here, the entire thermopile 4 is positioned on one side of the interface area 3. In the displayed embodiment, the thermopile 4 is positioned within the second phase 2. Depending on the properties of the phases 1, 2, however, it can also be advantageous to position the thermopile 4 on the other side of the interface area 3 within the solid or liquid first phase 1. As shown, the first portion 7 of the thermopile 4 is closer to the interface area 3 than the second portion 8 of the thermopile 4. Preferably, the first portion 7 of the thermopile 4 is installed directly at or on the interface area 3.

In the variants shown in FIGS. 1A and 1B, the first 7 and second portions 8 of the thermopile 4 are spaced from one another in a direction that is perpendicular to the interface area 3 for detection of the temperature difference. FIG. 1C shows an alternative variant (type C) of positioning the thermopile 4 at the interface area 3 in a top view onto the interface area 3, in which this is not the case. Here, the first 7 and second portions 8 of the thermopile 4 are located in a common plane that is parallel to the interface area 3. A measurement of the transition rate between the phases 1, 2 is now enabled by the phase transition being suppressed at the first portion 7 of the thermopile 4. Therefore, the interface area 3 is covered with a cover 10 in a region that corresponds to the first portion 7 of the thermopile 4. Preferably, the cover 10 is not or only to a limited extent permeable for the material. Hence, no or only a small quantity of material can pass between the first phase 1 and the second phase 2 in the covered area. A low effect of the latent heat or no effect at all therefore exists in the covered area. As, however, the interface area 3 is not covered at the second portion 8 of the thermopile 5, a phase transition is possible there. At the second portion 8 of the thermopile 4, latent heat is consequently released or extracted as a function of the transition rate of the phase transition. Hence, also in this version, conclusions can be drawn about the transition rate between the phases 1, 2 by measuring a temperature difference between the first 7 and second portions 8 of the thermopile 4. A particularly advantageous aspect is that a measurement of the type C will even be possible in an unaltered way if there is a variable external temperature gradient that is perpendicular to the interface area 3.

A simple application of the measurement methods displayed in the FIGS. 1A, 1B and 1C is for example the determination of the evaporation rate of a liquid such as water or alcohol under certain conditions. Such a measurement can be performed particularly easily with the variant (type A) shown in FIG. 1A. Here, the thermopile 4 only has to be sunk with its first portion 7 into the liquid (phase 1) whereas the second portion 8 protrudes out of the liquid into the gaseous phase (second phase 2). However, it is also possible to use measurements of the variants type B and type C to determine the evaporation speed of a liquid.

Figure 3A:
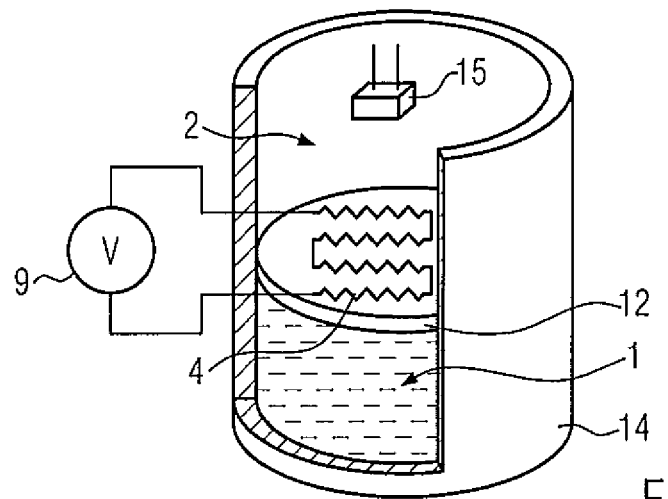
FIG. 3A a schematic display of a measurement according to an embodiment that allows for determining a permeability of a separation layer.

FIG. 3A schematically displays a special application of the measurement method according to the invention for determining a permeability of a separation layer 12 to be characterized. The separation layer 12 can for example be a plastic film, in particular a plastic film with breathing holes, a plastic material or a textile layer. A first phase 1 of the material, in relation to which the permeability of the separation layer 12 is to be determined, is put into a container 14 (shown in a section view for enhanced clarity) for measurement and subsequently covered with the separation layer 12. The separation layer 12 now forms the interface area 3 between the first phase 1 and a gaseous layer (second phase 2) of the material that is provided above the separation layer 12.

For determining the permeability, a measurement of the transition rate between the first phase 1 and the second phase 2 of the material is at first performed by means of the method according to the invention. For that, the thermopile 4 is provided on the separation layer 12. This can occur according to the variants (type A, type B or type C) described above. Here, an arrangement of the thermopile 4 according to the variants type B or type C displayed in the FIGS. 1B and 1C is particularly suitable. Also the variant shown in FIG. 1A would be possible in principle. In this context, however, attention needs to be paid that the thermopile 4 has to penetrate the separation layer 12 to be examined and that consequently the permeability of the separation layer 12 to be measured can be distorted at the respective penetration points.

Based on the measured thermoelectric voltage, the permeability of the separation layer 12 can be determined via Darcy's law. As described above, it is expressed as $V_t = k \cdot (p_2 - p_1)$ with $V_t$ being the transition rate from the first phase 1 to the second phase 2, $p_1$ the pressure potential of the first phase, $p_2$ the pressure potential of the second phase and $k$ a proportionality factor that represents the permeability of the separation layer 12 between the phases 1, 2. The transition rate $V_t$ can be determined out of the measured thermoelectric voltage. To determine the proportionality factor $k$ that represents the permeability of the separation layer 12, the pressure potentials $p_1$, $p_2$ of the two phases are required in addition. The pressure potential $p_2$ of the gaseous phase is determined preferably by means of a temperature and moisture measurement as described above. Therefore, a temperature and moisture sensor 15, which may for example be attached at the container 14, can be provided within the gaseous phase. The pressure potential $p_1$ of the first phase 1 can be measured as well. Preferably, however, this pressure potential is known anyway, for example when the material exists simply as a pure liquid in the first phase 1.

Figure 3B:
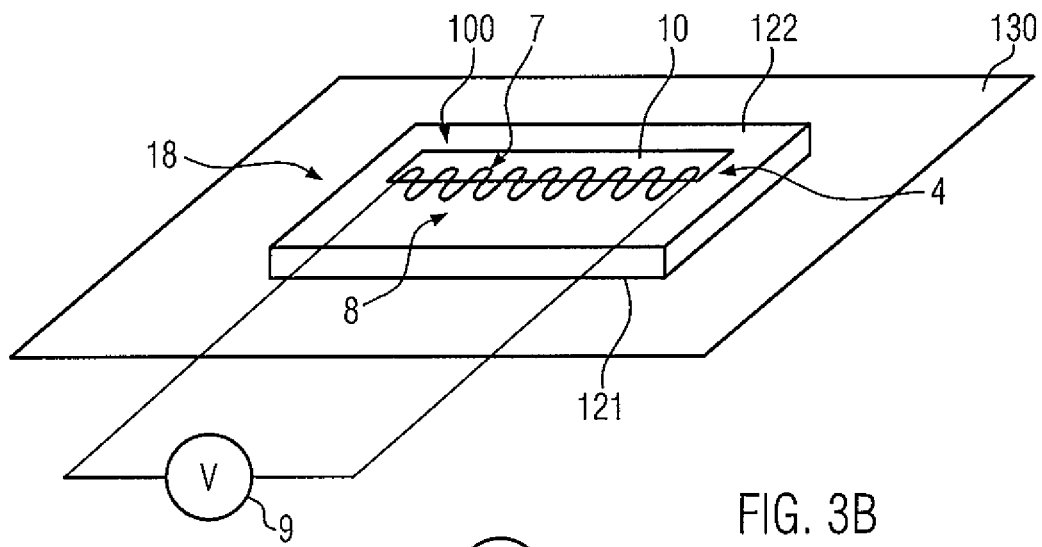
FIG. 3B a schematic display of a device according to an embodiment with an anhesive layer.

A further application of the measurement method according to the invention and a respective device 18 are shown in FIG. 3B. The device 18 comprises an adhesive layer 100 with a lower side 121 and an upper side 122. With the lower side 121, the adhesive layer 100 can be installed fast and simply at an interface area 3 to be measured between a first phase 1 and a second phase 2. In the shown example, the lower side 121 of the adhesive layer 100 is attached at the skin surface 130 of a user in order to measure the user's transpiration rate. A respective device 18 could for example be used for sports or for medical purposes. The lower side 121 of the bonding layer 110 could also be installed on a part of a plant, e.g. on a leaf. The thermopile 4 is installed at the adhesive layer 100, in particular on its upper side 122, so that the transition rate between the phases can be determined based on the thermoelectric voltage. In the shown embodiment, the first portion 7 and the second portion 8 of the thermopile 4 are located in a common plane that is parallel to the upper side 121 of the adhesive layer 100. In addition, a cover 10 is provided that covers the adhesive layer 100 at the first portion 7 of the thermopile 4, but not at the second portion 8 of the thermopile 4. Hence, the shown device 18 is designed for measurements of type C. But it would also be conceivable to install the thermopile 4 at the adhesive layer 100 in such a way that measurements of types A or B are possible. It is conceivable for the adhesive layer 100 to have a certain thickness to increase the stability of the device. However, the adheive layer 100 could also be formed only as a very thin adhesive layer that allows for an attachment of the thermopile 4 but that does not significantly affect the permeability of the interface area 3. In particular, it is not necessary for the adhesive layer 100 to form a continuous layer. It would be conceivable for the adhesive layer to cover only certain areas of the thermopile 4 that are relevant for attachment.

Figure 3C:
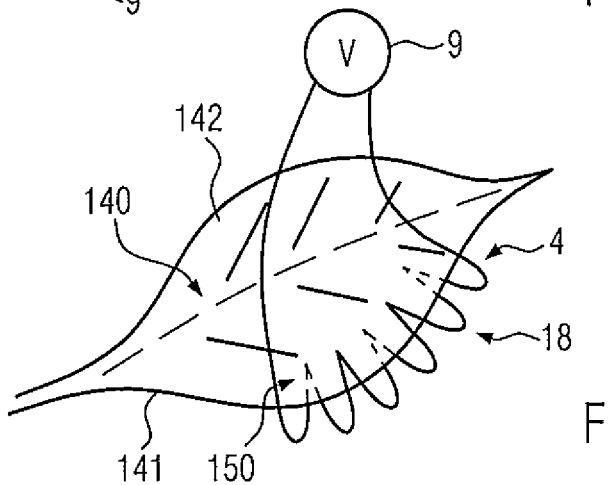
FIG. 3C a schematic display of a device according to an embodiment that is suitable in particular for measuring the transpiration rate of a plant leaf.

FIG. 3C shows a further application of the measurement method according to the invention and a respective device 18. The shown device 18 is particularly suitable for measuring a transpiration rate of a plant leaf 140. According to this embodiment, the device 18 comprises a particularly formed thermopile 4. Between the first portion 7 and the second portion 8 of the thermopile 4, a slit 150 is provided to receive the plant leaf 140. When the plant leaf 140 is inserted, the first portion 7 of the thermopile 4 is adjacent to the lower leaf side 141 and the second portion 8 of the thermopile 4 is adjacent to the upper leaf side 142. As plant leaves 140 typically transpire only on one side (usually on the underside 141), a temperature difference between the upper leaf side 142 and the lower leaf side 141, which arises due to the latent heat of the phase transition through the transpiration on only one leaf side 141, can be measured based on the thermoelectric voltage on the thermopile 4. Therefore, the transpiration rate of the leaf 140 can be determined. Of course, also other samples that show transpiration on only one side can be examined with the device 18.

Figure 3D:
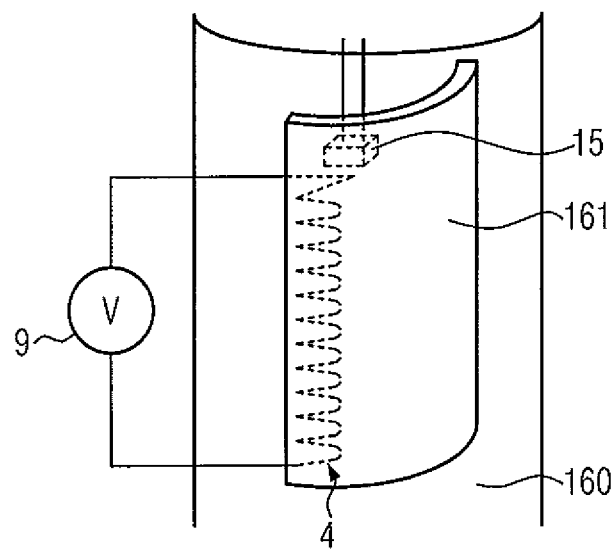
FIG. 3D shows an application of the measurement method according to the invention for measuring the water potential in a tree trunk.

FIG. 3D shows the application of the measurement method according to the invention for measuring the water potential in a tree trunk. A thermopile 4 of type C is installed at the bark 160 of the tree. The thermopile 4 is protected against rain and weather effects by means of a cap 161. Based on the thermoelectric voltage of the thermopile 4, the transition rate from a liquid phase within the tree trunk to a gaseous phase that exists outside can be determined. If a moisture and temperature sensor 15 is provided within the cap 161 in addition, the water potential within the tree trunk can be determined as well.

In practice, it can happen that no natural interface area exists between a solid or liquid phase and a gaseous phase in a system to be measured, but only a gaseous phase in a first region 31 and a gaseous phase in a second region 32. In this case, a liquid phase 1 and hence an interface area 3 between such liquid phase and one of the gaseous phases can be artificially created through a porous substrate plate 20 (with open pores) with a lower side 21 and an upper side 22. This method is based on the situation that gaseous material (steam) condenses more easily within the porous substrate plate 20 due to effects of surface tension. This effect scales with the diameter of the pores 25 of the substrate plate 20. The substrate plate 20 should of course be permeable for the material. This can be achieved by the substrate plate 20 having continuously interconnected pores 25 from its upper side 22 to its lower side 21 through which the material can pass. Alternatively, the pores 25 can for example be provided only on the lower side 21 and/or the upper side 22 of the substrate plate 20, in particular as open pores 25. In this case, the substrate plate 20 can be made of a raw material that is permeable for the material or comprise such a raw material.

One of the two sides 21, 22 of the substrate plate 20 faces the first region 31 and the other side 21, 22 faces the second region 32. To diffuse between the first and second regions 31, 32, the material therefore has to pass the porous substrate plate 20. In this process, the material condenses within the substrate plate 20 so that a liquid phase 1 is created artificially there. Then, the transition rate from this liquid phase (first phase 1) into the gaseous phase (second phase 2) of a region 31, 32 can be determined by means of a thermopile 4 similarly to the method described above. This transition rate allows for determining the transition rate between the two regions 31, 32. Hence, a transition rate between a (artificially created) first, solid or liquid, phase 1 and a second, gaseous, phase 2 of a material is essentially measured also in this case.

The transition rate between the phases 1, 2 can be measured with a thermopile 4 provided on the substrate plate 20 in accordance with the principles described above. It is particularly advantageous if the thermopile 4 is already integrated firmly in the porous substrate plate 20 and/or attached to the substrate plate so that the orientation and positioning of the thermopile 4 in relation to the substrate plate 20 is clearly defined and constant. As also the permeability properties of the porous substrate plate 20 are constant, calibration measurements performed just once and reference data obtained from such measurements can be used for multiple measurements in a simple way.

Figure 2A:
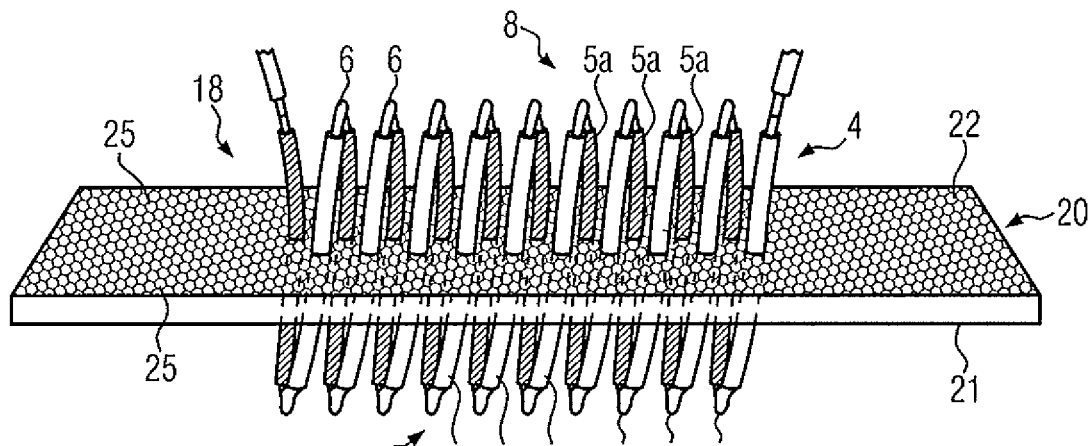
FIG. 2A a schematic perspective view of a device according to an embodiment of type A.
Figure 2B:
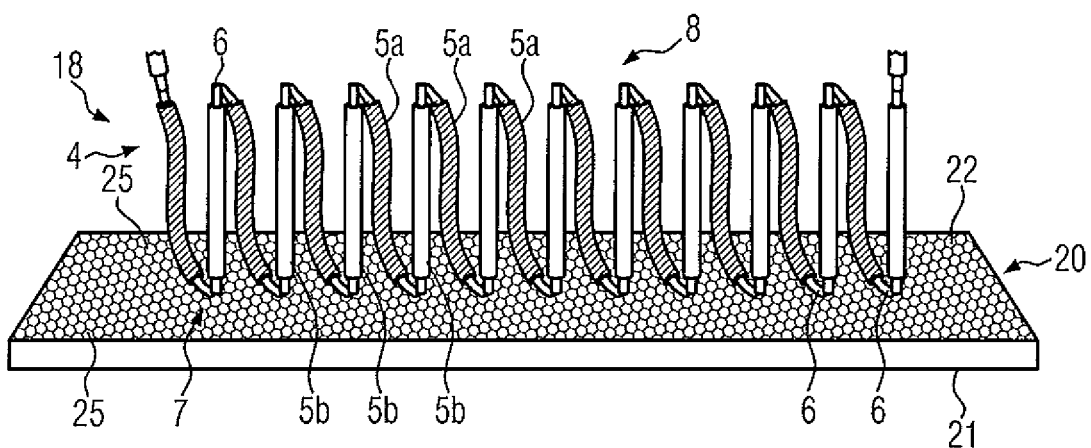
FIG. 2B a schematic perspective view of a device according to an embodiment of type B.
Figure 2C:
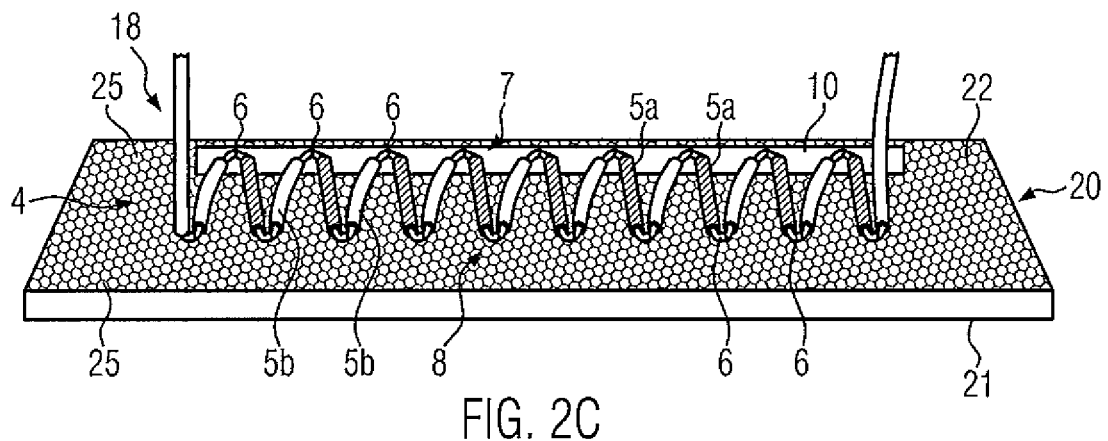
FIG. 2C a schematic perspective view of a device according to an embodiment of type C.

FIGS. 2A, 2B and 2C show different variants of a device 18 according to the invention with a porous substrate plate 20 for creating an artificial interface area 3 and a thermopile 4 installed on it. The variants differ from each other in the arrangement of the thermopile 4 in relation to the porous substrate plate 20.

To be able to perform measurements of type A, the first portion 7 of the thermopile 4 is provided on the lower side 21 of the substrate plate 20 and the second portion 8 of the thermopile 4 is provided on the upper side 22 of the substrate plate 20 (device type A) according to the variant of the device shown in FIG. 2A.

To be able to perform measurements of type B, the thermopile 4 is, according to the variant of the device 18 shown in FIG. 2B (device type B), located completely on the upper side 22 of the substrate plate 20 with the first portion 7 of the thermopile 4 being located more closely to the upper side 22 of the substrate plate 20 than the second portion 8 of the thermopile 4. Alternatively, the thermopile 4 can be located completely on the lower side 21 of the substrate plate 20 with the first portion 7 of the thermopile 4 being located more closely to the lower side 21 of the substrate plate 20 than the second portion 8 of the thermopile 4. In particular, the first portion 7 of the thermopile 4 can be attached directly on the porous substrate plate 20.

To be able to perform measurements of type C, the first 7 and second portions 8 of the thermopile 4 are located, according to the variant of the device 18 shown in FIG. 2C, in a common plane that is parallel to the lower side 21 and/or the upper side 22 of the substrate plate (device type C). In the shown embodiment, the thermopile 4 is installed flatly on the upper side 22 of the substrate plate 20. Alternatively, the thermopile 4 can be installed flatly a the lower side 21 of the substrate plate 20. A device 18 according to type C also comprises the cover 10 described above that covers the porous substrate plate 20 at the first portion 7 of the thermopile 4 but not at the second portion 8 of the thermopile 4. In the shown embodiment, the cover 10 is provided between the substrate plate 20 and the first portion 7 of the thermopile 4. But the cover 10 could also be provided on the side of the thermopile 4 that is opposite to the substrate plate 20. In particular, the cover 10 can be attached on the porous substrate plate 20 and/or on the thermopile 4.

Figure 3E:
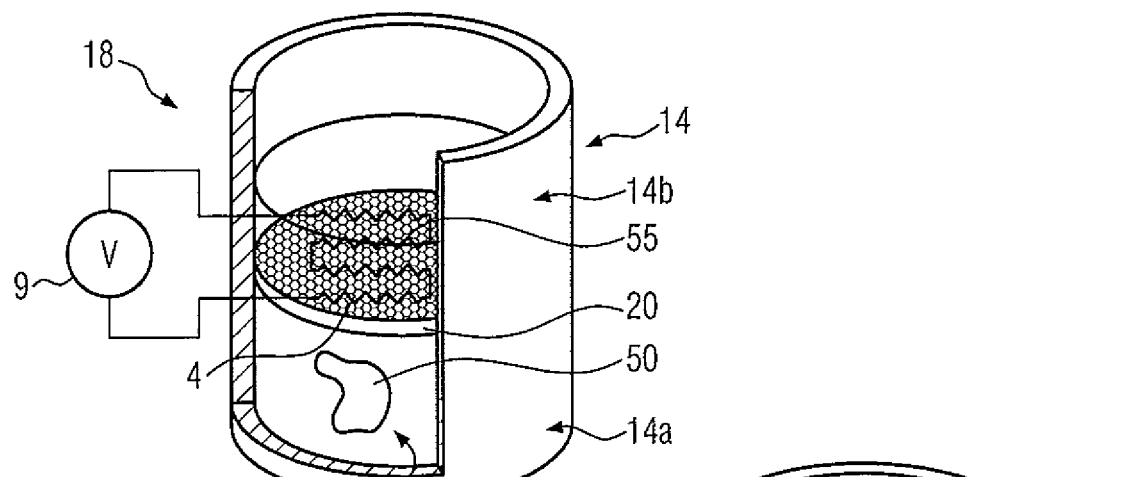
FIG. 3E a schematic display of a device according to an embodiment that is suitable in particular for determining the water potential of a sample.
Figure 3F:
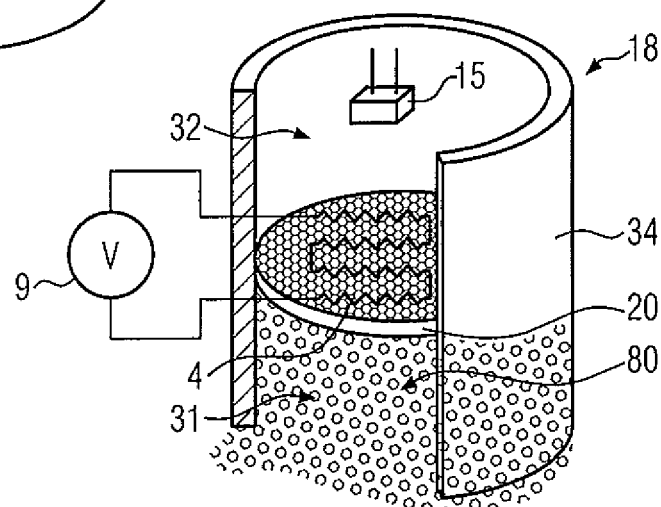
FIG. 3F a schematic display of a device according to an embodiment that is suitable in particular for determining the water potential of a ground.

FIGS. 3E and 3F show embodiments of a device 18 according to the invention in which the porous substrate plate 20 is integrated in a defined measurement environment.

The embodiment displayed in FIG. 3F is particularly suitable for determining the water potential of a ground 80. The device 18 shown herein comprises a tube 34 (displayed as a section view for better clarity). The porous substrate plate 20 with the thermopile 4 (type A, type B or type C) is provided or installed in the tube 34 in such a way that it divides the tube 34 into two axially successive sections (upper and lower section). A temperature and moisture sensor 15 is provided in the upper section. For the measurement, the tube 34 is simply inserted up to the substrate plate 20 into the ground 80 to be measured and the thermoelectric voltage on the thermopile 4 is measured subsequently. In the ground section that exists in the inserted lower section of the tube 34, the water is typically in a gaseous state (first region 31). In the upper section of the tube 34 that protrudes out of the ground 80, the water is also gaseous in form of atmospheric humidity (second region 32). As described above, a phase of liquid water is formed due to the porous structure in the porous substrate plate 20. Therefore and as also described above, the transition rate of water between the first region 31 in the lower section of the tube 34 (ground 80) and the second region 32 in the upper section of the tube 34 (air) can be measured (indirectly via the transition rate from or into the artificially created liquid phase) by means of measuring the thermoelectric voltage at the thermopile 4. This is evidently an example for a measurement of a transition rate of water between two regions 31, 32, in which water is in a gaseous state. The water potential in the second region 32 (air above the ground 80) can be determined based on a temperature and moisture measurement in the part of the tube 34 that protrudes out of the ground 80. Hence, a determination of the water potential of the ground 80 will then be possible in consideration of the measured thermoelectric voltage.

To perform other measurements, the device 18 can, as shown in FIG. 3E, comprise a container 14 (displayed as a section view for better clarity) with a ground 30 as an alternative to the tube 34. The substrate plate 20 with the thermopile 4 (type A, type B or type C) can be provided or installable in the container 14 in a way that it divides the absorption volume of the container 14 into a lower part 14a, which comprises the ground 30 of the container 14, and an upper, in particular open, part 14b. The lower part 14a of the container 14 can be designed for receiving a sample 50 (plants, ground, medicines, foods, etc.) whose water potential is to be determined. After a certain time, an equilibrium will be formed and the water potential of the sample 50 will be equivalent to the water potential of the gaseous phase in the lower part 14a of the container 14. A water layer 55 is inserted in the upper part 14b of the container 14. The substrate plate 20 separates the gaseous phase (second phase 2) in the lower part 14a of the container 14 from the water layer 55 (first phase 1) in the upper part. The transition rate between the phases 1, 2 can be determined by measuring the thermoelectric voltage of the thermopile 4 that is provided on the substrate plate 20. This application is an example for the use of the porous substrate plate 20 without this substrate plate creating a liquid phase artificially. An advantage of providing the water layer 55 in the upper part 14b of the container 14 is that the water potential in the upper part 14b of the container 14 is set to a known value, in particular to zero. Therefore, no moisture and temperature meter has to be provided to determine the water potential of the sample 50.

In the FIGS. 3A, 3E and 3E, the thermopile 4 is displayed schematically as a sequence of multiple shorter thermopiles 4 that are connected in a row. This can for example be advantageous if a porous substrate plate 20 having a defined form is to be used as completely as possible for the measurement. Arrangements of the thermopile 4 according to all presented variants (type A, type B or type C) are possible respectively for the shown applications. If a thermopile 4 according to type C that is composed of multiple shorter thermopiles 4 is to be positioned at the interface area 3, multiple covers 10 can be used according to the multiple shorter thermopiles 4.

The invention claimed is:

1. A device for measuring a transition rate between a first phase of a material and a second phase of the material, wherein the material is solid or liquid in the first phase and gaseous in the second phase, the device comprising:
    a porous substrate plate with a lower side and an upper side, the porous substrate plate being permeable for the material; and
    a thermopile installed at the porous substrate plate and with a plurality of conductor transitions, wherein the thermopile has a first portion, which comprises every second one of the conductor transitions, and a second portion, which comprises the remaining conductor transitions, and is configured to output a measurable thermoelectric voltage that represents a temperature difference between the first and the second portion of the thermopile.

2. The device according to claim 1, wherein the first portion of the thermopile is provided on the lower side of the substrate plate and the second portion of the thermopile on the upper side of the substrate plate.

3. The device according to claim 1, wherein the thermopile is located completely on the lower side or on the upper side of the substrate plate, and wherein the first portion of the thermopile is closer to the respective side of the substrate plate than the second portion of the thermopile.

4. The device according to claim 1, wherein the first portion and the second portion of the thermopile are located in a common plane that is parallel to the lower side and/or the upper side of the substrate plate, and wherein a cover is provided that covers the porous substrate plate at the first portion of the thermopile but not at the second portion of the thermopile.

5. The device according to claim 1 further comprising a container with a floor, wherein the porous substrate plate is configured to be installed in the container in a way that the porous substrate plate divides the receiving volume of the container into a lower part that comprises the floor and an upper part.

6. The device according to claim 1 further comprising a tube, wherein the porous substrate plate is installed in the tube in a way that the porous substrate plate divides the tube into two axially successive sections.

7. The device according to claim 1 further comprising a moisture and temperature sensor.

8. The device according to claim 1, wherein the porous substrate plate has a mean pore diameter of less than 100 µm, less than 50 µm, less than 10 µm, less than 1 pm or less than 800 nm or a mean pore diameter between 200 nm and 800 nm, between 500 nm and 2 µm or between 200 nm and 5 µm.

9. A method for measuring a transition rate between a first phase of a material and a second phase of the material with the material being solid or liquid in the first phase and gaseous in the second phase with the device according to claim 1, the method comprising:

artificially creating the first phase through the porous substrate plate;

providing the thermopile at an interface area between the first and the second phase; and measuring a thermoelectric voltage of the thermopile, which represents a temperature difference between the first and the second portion of the thermopile.

10. The method according to claim 9, wherein the thermopile is integrated firmly in the porous substrate plate or attached to the porous substrate plate.

11. The method for determining a pressure potential, comprising:

carrying out the method according to claim 9; and determining the pressure potential of the first phase of the material or the second phase of the material based on a known or measured value of the pressure potential of the other phase of the material and the measured thermoelectric voltage.

12. The method for determining a permeability of a separation layer, comprising:

carrying out the method according to claim 9 while the separation layer is located between the first phase and the second phase;

determining the permeability of the separation layer based on the measured thermoelectric voltage and known or measured values of the pressure potential of the two phases of the material.

13. The method according to claim 9, wherein the method is used for measuring a transpiration rate of a living being, for measuring an evaporation rate of a ground or for determining the water potential or the permeability of a material composition.

14. A use of the device according to claim 1 for measuring a transpiration rate of a living being, for measuring an evaporation rate of a ground or for determining the water potential or the permeability of a material composition.

\* \* \* \* \*